United States Patent
Yau et al.

(10) Patent No.: US 9,226,411 B2
(45) Date of Patent: *Dec. 29, 2015

(54) MAKING MULTI-LAYER MICRO-WIRE STRUCTURE

(71) Applicant: Eastman Kodak Company, Rochester, NY (US)

(72) Inventors: Hwei-Ling Yau, Rochester, NY (US); David Paul Trauernicht, Rochester, NY (US); John Andrew Lebens, Rush, NY (US); Yongcai Wang, Rochester, NY (US); Ronald Steven Cok, Rochester, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/326,806

(22) Filed: Jul. 9, 2014

(65) Prior Publication Data

US 2014/0322436 A1    Oct. 30, 2014

Related U.S. Application Data

(63) Continuation of application No. 13/779,939, filed on Feb. 28, 2013, now Pat. No. 8,828,503.

(51) Int. Cl.
*B05D 3/06* (2006.01)
*H05K 3/46* (2006.01)
*G06F 3/044* (2006.01)

(52) U.S. Cl.
CPC ............... *H05K 3/467* (2013.01); *G06F 3/044* (2013.01)

(58) Field of Classification Search
CPC ..... H05K 3/107; H05K 3/467; H05K 3/4644; H05K 3/1258

See application file for complete search history.

(56) References Cited

U.S. PATENT DOCUMENTS

| 8,179,381 | B2 | 5/2012 | Frey et al. | |
|---|---|---|---|---|
| 8,828,503 | B1* | 9/2014 | Yau | G06F 3/044 427/271 |
| 2004/0213962 | A1 | 10/2004 | Bourdelais et al. | |
| 2007/0281136 | A1 | 12/2007 | Hampden-Smith et al. | |
| 2008/0257211 | A1 | 10/2008 | Oriakhi | |
| 2010/0328248 | A1 | 12/2010 | Mozdzyn | |
| 2012/0147120 | A1 | 6/2012 | Khan et al. | |
| 2014/0306382 | A1* | 10/2014 | Cok | G06F 3/044 264/447 |

FOREIGN PATENT DOCUMENTS

| CN | 102063951 | 5/2011 |
|---|---|---|
| WO | 03/032084 | 4/2003 |
| WO | 2012/168941 | 12/2012 |

* cited by examiner

*Primary Examiner* — Michael Wieczorek
(74) *Attorney, Agent, or Firm* — Raymond L. Owens

(57) ABSTRACT

A method of making a multi-layer micro-wire structure includes providing a substrate having a surface and forming a plurality of micro-channels in the surface. A first material composition is located in a first layer only in each micro-channel and not on the surface. A second material composition different from the first material composition is located in a second layer different from the first layer only in each micro-channel and not on the surface. The first material composition in the first layer and the second material composition in the second layer form an electrically conductive multi-layer micro-wire in each micro-channel.

15 Claims, 16 Drawing Sheets

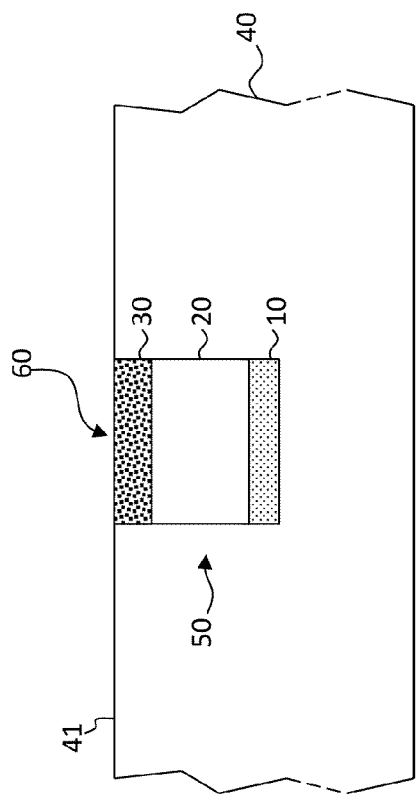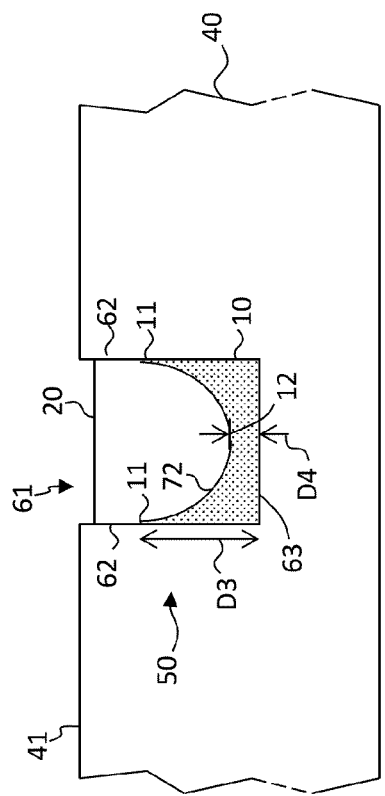

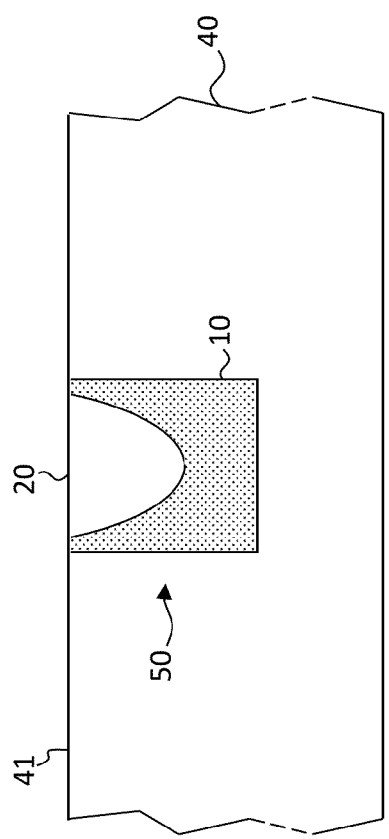
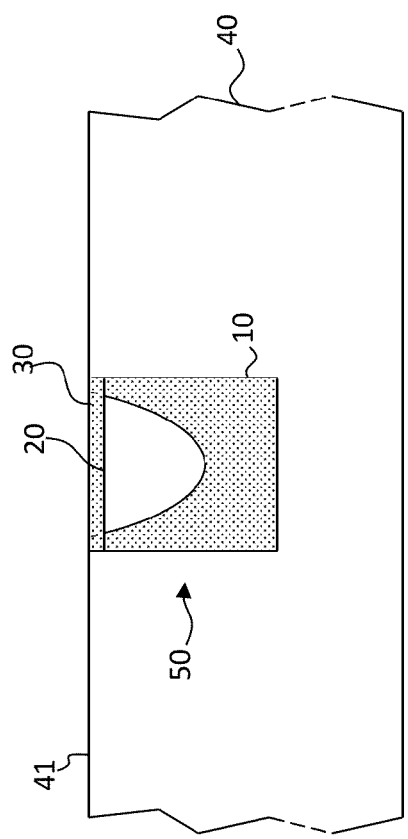

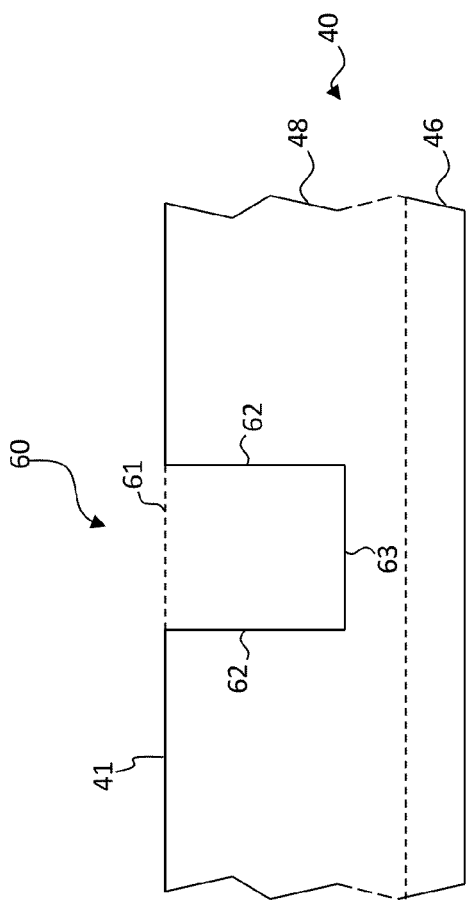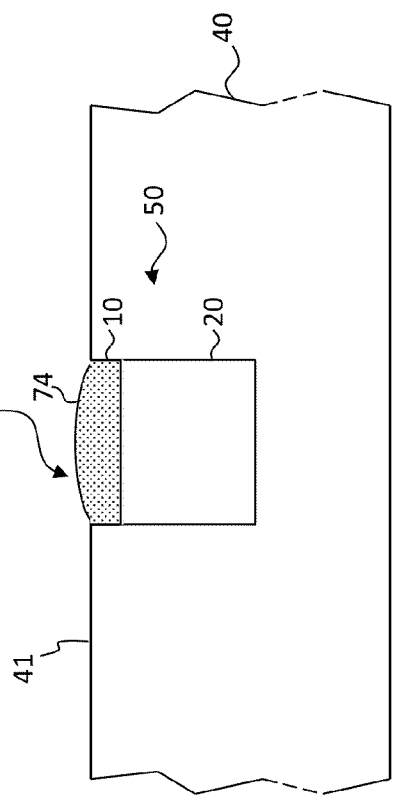

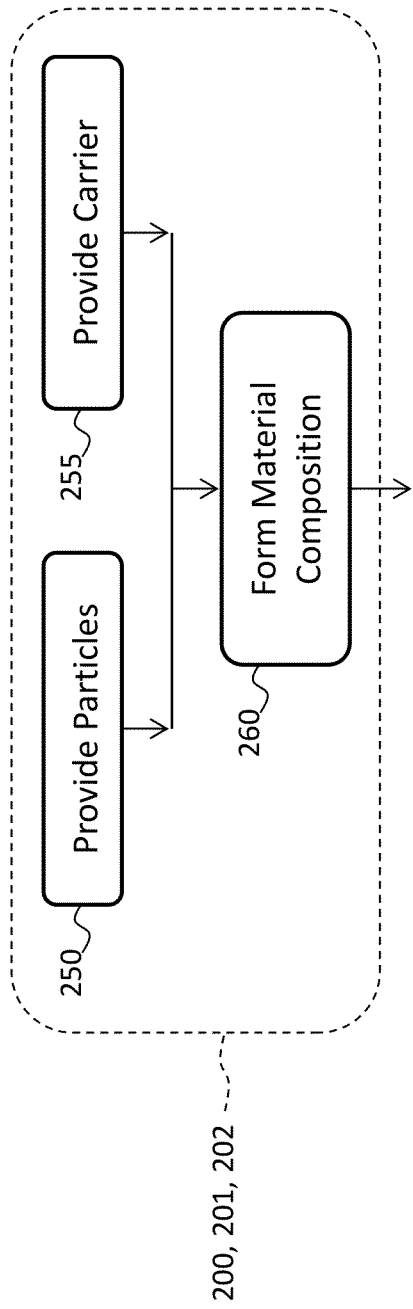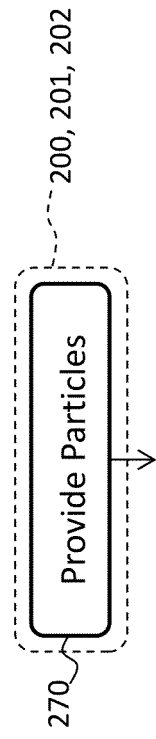

MAKING MULTI-LAYER MICRO-WIRE STRUCTURE

CROSS REFERENCE TO RELATED APPLICATIONS

This application is a continuation of commonly-assigned U.S. patent application Ser. No. 13/779,939 (now U.S. Pat. No. 8,828,503), filed Feb. 28, 2013, the disclosure of which is incorporated herein.

Reference is made to commonly-assigned U.S. patent application Ser. No. 13/779,917 filed Feb. 28, 2013, entitled "Multi-Layer Micro-Wire Structure" by Yau et al, the disclosure of which is incorporated herein.

FIELD OF THE INVENTION

The present invention relates to micro-wire electrical conductors.

BACKGROUND OF THE INVENTION

Transparent conductors are widely used in the flat-panel display industry to form electrodes for electrically switching the light-emitting or light-transmitting properties of a display pixel, for example in liquid crystal or organic light-emitting diode displays. Transparent conductive electrodes are also used in touch screens in conjunction with displays. In such applications, the transparency and conductivity of the transparent electrodes are important attributes. In general, it is desired that transparent conductors have a high transparency (for example, greater than 90% in the visible spectrum) and a low electrical resistivity (for example, less than 10 ohms/square).

Conventional transparent conductors are typically coated on a substrate to form a patterned layer of a transparent, conductive material, such as indium tin oxide or other metal oxide. Such materials are increasingly expensive and relatively costly to deposit and pattern. Moreover, metal oxides have a limited conductivity and transparency, and tend to crack when formed on flexible substrates.

More recently, transparent electrodes including very fine patterns of conductive micro-wires have been proposed. For example, capacitive touch-screens with mesh electrodes including very fine patterns of conductive elements, such as metal wires or conductive traces, are taught in U.S. patent application Publication No. 2010/0328248 and U.S. Pat. No. 8,179,381, which are hereby incorporated in their entirety by reference. As disclosed in U.S. Pat. No. 8,179,381, fine conductor patterns are made by one of several processes, including laser-cured masking, inkjet printing, gravure printing, micro-replication, and micro-contact printing. The transparent micro-wire electrodes include micro-wires between 0.5 g and 4 g wide and a transparency of between approximately 86% and 96%.

Conductive micro-wires can be formed in micro-channels embossed in a substrate, for example as taught in CN102063951, which is hereby incorporated by reference in its entirety. As discussed in CN102063951, a pattern of micro-channels can be formed in a substrate using an embossing technique. Embossing methods are generally known in the prior art and typically include coating a curable liquid, such as a polymer, onto a rigid substrate. The polymer is partially cured (through heat or exposure to light or ultraviolet radiation) and then a pattern of micro-channels is embossed (impressed) onto the partially cured polymer layer by a master having a reverse pattern of ridges formed on its surface. The polymer is then completely cured. A conductive ink is then coated over the substrate and into the micro-channels, the excess conductive ink between micro-channels is removed, for example by mechanical buffing, patterned chemical electrolysis, or patterned chemical corrosion. The conductive ink in the micro-channels is cured, for example by heating. In an alternative method described in CN102063951, a photosensitive layer, chemical plating, or sputtering is used to pattern conductors, for example using patterned radiation exposure or physical masks. Unwanted material (photosensitive resist) is removed, followed by electro-deposition of metallic ions in a bath.

Optical attributes such as transparency, contrast, or reflectivity are important for display systems. Mechanical concerns such as flexibility and environmental robustness such as scratch and chemical resistance are also important, especially for touch screens designed for interaction with humans. There is a need, therefore, for improved micro-wire structures that meet these needs.

SUMMARY OF THE INVENTION

In accordance with the present invention, a method of making a multi-layer micro-wire structure comprises:
  providing a substrate having a surface;
  forming a plurality of micro-channels in the surface;
  locating a first material composition in a first layer in each micro-channel and not on the surface;
  locating a second material composition different from the first material composition in a second layer different from the first layer in each micro-channel and not on the surface; and
  wherein the first material composition in the first layer and the second material composition in the second layer form an electrically conductive multi-layer micro-wire in each micro-channel.

The present invention provides an electrically conductive micro-wire structure having improved transparency, contrast, or reflectivity, improved flexibility, and resistance to scratches.

BRIEF DESCRIPTION OF THE DRAWINGS

The above and other features and advantages of the present invention will become more apparent when taken in conjunction with the following description and drawings wherein identical reference numerals have been used to designate identical features that are common to the figures, and wherein:

FIGS. 2-10 are cross sections of a multi-layer micro-wire in a micro-channel illustrating other embodiments of the present invention;

FIGS. 15-20 are flow charts illustrating various methods of making the present invention;

Figure 1:
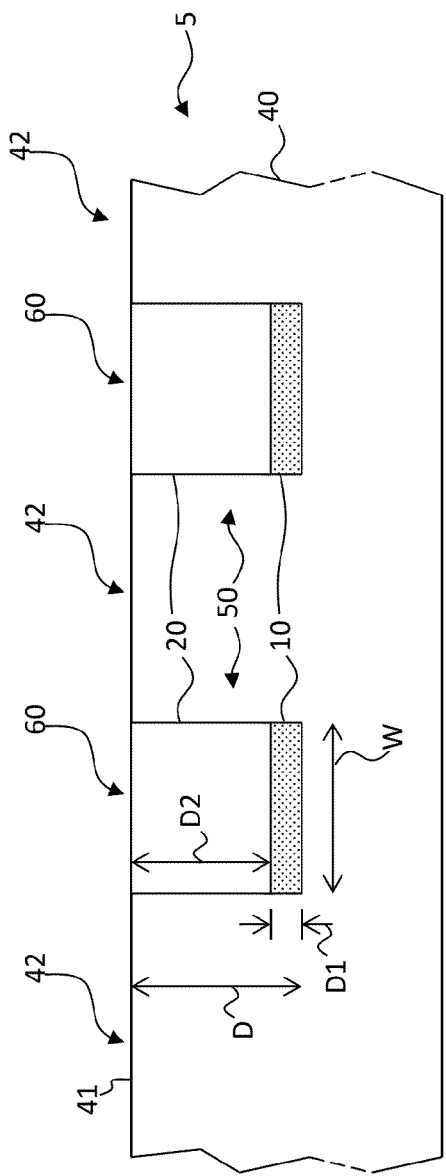
FIG. 1 is a cross section of a multi-layer micro-wire structure embodiment of the present invention.

The Figures are not necessarily to scale, since the range of dimensions in the drawings is too great to permit depiction to scale.

DETAILED DESCRIPTION OF THE INVENTION

The present invention is directed toward multi-layer micro-wire structures formed in a substrate that are capable of conducting electrical currents. The electrically conductive micro-wire structures provide improved transparency, contrast, or reflectivity, improved flexibility, and resistance to scratches.

Referring to FIG. 1 in an embodiment of the present invention, a multi-layer micro-wire structure 5 includes a substrate 40 having a substrate surface 41. A plurality of micro-channels 60 are formed in substrate 40. Substrate-surface open areas 42 on substrate 40 separate micro-channels 60. Micro-channels 60 extend from substrate surface 41 into substrate 40. A first material composition is located in a first layer 10 in each micro-channel 60 and not on substrate surface 41 and not in substrate-surface open areas 42 between micro-channels 60. A second material composition different from the first material composition is located in a second layer 20 different from first layer 10 in each micro-channel 60 and not on substrate surface 41 and not in substrate-surface open areas 42 between micro-channels 60. The first material composition in first layer 10 and the second material composition in second layer 20 form an electrically conductive multi-layer micro-wire 50 in each micro-channel 60.

The designation of first or second with respect to material compositions or layers is arbitrary and does not necessarily specify order or structure. Thus, depending on the embodiment of the present invention, first layer 10 is formed on second layer 20 or second layer 20 is formed on first layer 10. In any specific example or embodiment, the first or second material composition or layer designations can be reversed without changing the nature of the invention.

According to various embodiments of the present invention, the substrate 40 is any material having a substrate surface 41 in which micro-channels 60 can be formed. For example, glass and plastic are suitable materials known in the art from which substrates 40 can be made into sheets of material having substantially parallel opposed sides, one of which is substrate surface 41. In various embodiments, substrate 40 is rigid, flexible, or transparent. The substrate 40 of the present invention is large enough for a user to directly interact therewith, for example with an implement such as a stylus or with a finger or hand. The substrates of integrated circuits are too small for such interaction.

The micro-channel 60 is a groove, trench, or channel formed in substrate 40 and extending from substrate surface 41 into substrate 40 and having a cross-sectional width W in a direction parallel to substrate surface 41 less than 20 microns, for example 10 microns, 5 microns, 4 microns, 3 microns, 2 microns, 1 micron, or 0.5 microns, or less. In an embodiment, the cross-sectional depth D of micro-channel 60 is comparable to the width W. Micro-channels 60 can have a rectangular cross section, as shown. Other cross-sectional shapes, for example trapezoids, are known and are included in the present invention. First and second layers 10, 20 can have different depths, for example first layer 10 has a depth of D1 and second layer 20 has a second depth D2 that is greater than D1. As used herein, the depth of a layer (first and second layers 10, 20) or the depth of a multi-layer micro-wire 50 is also the thickness of the layer or micro-wire. The width or depth of a layer is measured in cross section.

Multi-layered micro-wires 50 of the present invention are structured micro-wires and have at least first and second layers 10, 20. Multi-layer micro-wires 50 having more than two layers, for example three layers, are also contemplated and are included in the present invention and discussed further below. At least one of first or second layers 10, 20 of multi-layer micro-wire 50 is electrically conductive. In an embodiment, more than one layer of multi-layer micro-wires 50 is electrically conductive, for example first and second layers 10, 20 are electrically conductive. In different embodiments, first layer 10 is more electrically conductive than second layer 20 or second layer 20 is more electrically conductive than first layer 10. First or second layer 10, 20 can have different optical properties.

Different materials coated in separate layers over patterned substrates are known. In contrast, multi-layer micro-wires 50 are formed in micro-channels 60 and not over the surface of the substrate 40. Because micro-channels 60 have such a narrow width and extend into substrate 40, conventional substrate deposition and patterning methods, for example using sputtering to form a layer and then coated photo-resist with masked exposure to pattern a substrate are problematic or expensive. While it is known to form conventional micro-wires, as discussed above, multi-layer micro-wires 50 of the present invention are structured multi-layer micro-wires 50 having at least first and second layers 10, 20. Such structured multi-layered micro-wires 50 are not known in the prior art and provide advantages as disclosed herein.

The first and second material compositions forming first and second layers 10, 20 are located in micro-channels 60 only, and are not located on substrate surface 41, for example between micro-channels 60 in substrate-surface open areas 42. Thus, first and second layers 10, 20 are found only in micro-channels 60 and not in substrate surface open areas 42. First or second material compositions can be provided in one state and then processed into another state, for example converted from a liquid state into a solid state, to form a layer. Such conversion can be accomplished in a variety of ways, for example by drying or heating. Furthermore, first or second material compositions can include a set of materials when located and be processed to include a subset of the set of materials, for example by removing solvents from the material composition. For example, a material composition including a solvent is deposited and then processed to remove the solvent leaving a material composition without the solvent in place. Thus, according to embodiments of the present invention, a material composition that is deposited on substrate 40 is not necessarily the same composition as that found in a processed layer (first or second layer 10, 20).

According to various embodiments of the present invention, the first and second layers 10, 20 of micro-wires 50 have different electrical, mechanical, optical, or chemical properties. In the embodiment illustrated in FIG. 1, multi-layer micro-wire 50 includes first layer 10 located farther from substrate surface 41 than second layer 20, second layer 20 is more electrically conductive than first layer 10, and first layer 10 is more light-absorbing than second layer 20. In the embodiment illustrated in FIG. 2, multi-layer micro-wire 50 includes first layer 10 located closer to substrate surface 41 of substrate 40 than second layer 20, second layer 20 is more electrically conductive than first layer 10, and first layer 10 is more light-absorbing than second layer 20.

Referring to FIG. 3, in an embodiment of the present invention, substrate 40 has a micro-channel 60 extending from substrate surface 41 in which multi-layer micro-wire 50 is formed. Multi-layer micro-wire 50 includes first layer 10, second layer 20, and a third layer 30. Third layer 30 is formed from a third material composition located in third layer 30 in each micro-channel 60 and not on substrate surface 41. Third material composition, in one embodiment, is different from both the first and second material compositions or, in another embodiment, is substantially the same as either the first or second material composition. In a particular embodiment, third layer 30 is formed from a third material composition that is substantially the same as the first material composition so first and third layers 10, 30 are similar and the first and third material compositions are located both above and below second layer 20. In an embodiment, second layer 20 is more electrically conductive than first and third layers 10, 30, and first and third layers 10, 30 are more light-absorbing than second layer 20.

Figure 2:
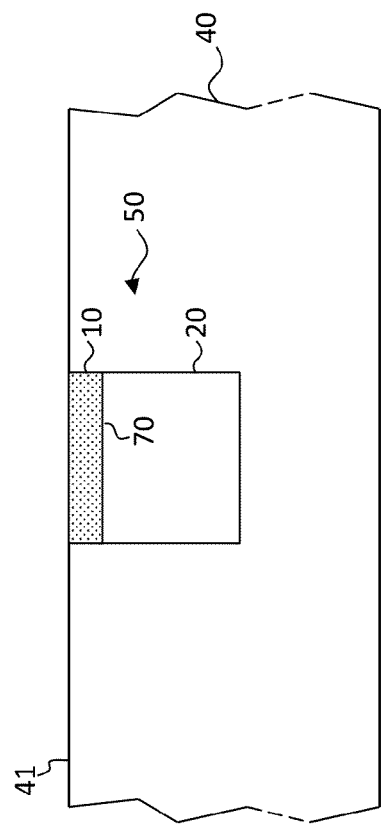

As shown in FIG. 2, first and second layers 10, 20 are in contact over a substantially flat surface 70. Referring to FIG. 4, in an embodiment of the present invention, multi-layer micro-wire 50 having first and second layers 10, 20 are in contact over a substantially curved surface 72. Referring also to FIG. 7, micro-channel 60 has a four-sided cross section with a micro-channel top 61 at substrate surface 41, a micro-channel bottom 63 opposing micro-channel top 61, and micro-channel sides 62 joining micro-channel top 61 to micro-channel bottom 63. As shown in FIG. 4, first layer 10 extends from locations 11 on micro-channel sides 62 that are relatively closer to micro-channel top 61 to a location 12 that is relatively closer to micro-channel bottom 63. A depth D3 of first layer 10 at micro-channel sides 62 is greater than a depth D4 of first layer 10 at location 12 nearer micro-channel bottom 63, forming curved surface 72 interfacing between first layer 10 and second layer 20 so that both first layer 10 and second layer 20 have a variable thickness.

In the embodiments illustrated in FIGS. 1-4, first and second layers 10 and 20 are essentially stacked so that second layer 20 is substantially above first layer 10 with respect to substrate surface 41 or vice versa. In an alternative embodiment illustrated in FIGS. 5 and 6, first and second layers 10 and 20 are at least partially concentric. By partially concentric is meant that one layer (second layer 20) is not exclusively over or under another layer (first layer 10). Referring to FIG. 5, multi-layer micro-wire 50 includes first layer 10 and second layer 20. First layer 10 is partially beneath second layer 20 (with respect to substrate surface 41 of substrate 40) and partially at the side of second layer 20. Thus, first layer 10 is not exclusively over or under second layer 10 since first layer 10 is also beside second layer 20. Therefore, in the example of FIG. 5, first layer 10 is partially concentric with second layer 20.

Referring to FIG. 6, multi-layer micro-wire 50 includes first layer 10 and second layer 20. First layer 10 is beneath second layer 20 (with respect to substrate surface 41 of substrate 40) and also at the side of second layer 20. Third layer 30 is over second layer 20 and has the same material composition as first layer 10. In such an embodiment, when the material compositions of two layers are the same, the layers can be considered to be one layer. Thus, first layer 10 is not exclusively over or under second layer 10 since first layer 10 is beside, under, and over second layer 20.

In various embodiments, first layer 10 or second layer 20 fills micro-channel 60 and extends to substrate surface 41 (as shown in FIGS. 1-3). Alternatively, first layer 10 or second layer 20 does not fill micro-channel 60 and extends beneath substrate surface 41 (as shown in FIG. 4). As shown in FIG. 8, in another embodiment of the present invention, first layer 10 or second layer 20 extends from micro-channel 60 beyond substrate surface 41 to form an extended surface 74 of multi-layer micro-wire 50 formed in substrate 40.

In various embodiments, first or second material compositions can include metal nano-particles. The metal nano-particles can be sintered to form a metallic electrical conductor. The metal can be silver or a silver alloy or other metals, such as tin, tantalum, titanium, gold, or aluminum, or alloys thereof. First or second material compositions can include light-absorbing materials such as carbon black, a dye, or a pigment. In one embodiment, the first material composition includes carbon black, a black dye, or a black pigment and the second material composition includes silver nano-particles.

In other embodiments, the second material composition includes a material in the first material composition or the first material composition includes a material in the second material composition. Alternatively, the first material composition can include two different materials in a first ratio and the second material composition can include the same two materials in a second ratio different from the first ratio. For example, the first material composition can include a relatively high percentage of a light-absorbing material such as carbon black and a relatively low percentage of metal nano-particles. In contrast, the second material composition can include a relatively low percentage of a light-absorbing material such as carbon black and a relatively high percentage of metal nano-particles. Note that both first and second layers, 10, 20 formed from the first and second material compositions, respectively, can be electrically conductive although in different amounts. As is known, carbon black itself can be conductive.

Figure 9:
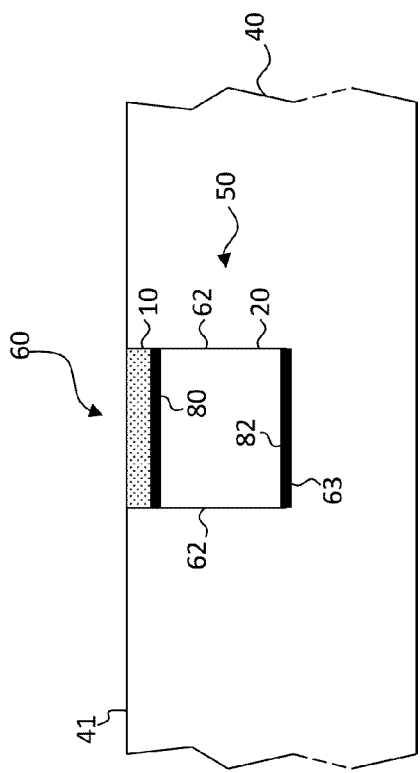

As noted above, multi-layer micro-wires 50 of the present invention can include more than two layers. Referring to FIG. 9, in one embodiment, the multi-layer micro-wire 50 including first and second layers 10, 20 is formed in substrate 40. A surface-energy layer 80 is located between first and second layers 10, 20. Surface energy layer 80 includes a material that controls the surface energy of the first material composition with respect to the second material composition. Thus, surface energy layer 80 can enable the first material composition to wet the second material composition in second layer 20. Surface-energy layer 80 can be deposited over second layer 20 before first layer 10 is located in micro-channel 60, for example by coating, and can, but does not necessarily, extend over substrate surface 41 of substrate 40. Alternatively, the surface of second layer 20 can be treated, for example with a plasma treatment, to modify its surface-energy characteristics and form the surface-energy layer 80.

In another embodiment, first layer 10 is adhered to substrate 40, second layer 20 is adhered to substrate 40, or first layer 10 is adhered to second layer 20. Adhesion between substrate 40 (for example in micro-channel 60 on either or both the micro-channel sides or bottom) is improved with an adhesion layer 82. Adhesion layer 82 can be located between first layer 10 and substrate 40 or between second layer 20 and substrate 40 (not shown). Adhesion layer 82 promotes adhesion between first layer 10 and substrate 40 or second layer 20 and substrate 40, or between first and second layers 10, 20. Adhesive materials are known in the art and can be coated or deposited. In an embodiment, adhesive materials are selected to complement first layer 10, second layer 20, or substrate 40.

First layer 10 or second layer 20 can have a color or be reflective. U.S. Patent Application Publication No. 2008/0257211 discloses a variety of metallic colored inks and its contents are hereby incorporated by reference.

Figure 10:
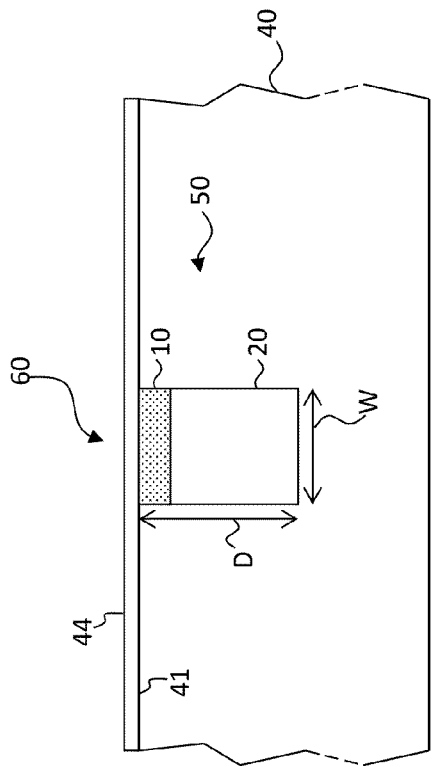

Referring further to FIG. 10, multi-layer micro-wire 50 including first and second layers 10, 20 formed in substrate 40 can have a width W less than a depth or thickness D so that multi-layer micro-wire 50 has an aspect ratio (D/W) greater than one. Multi-layer micro-wire 50 can be covered with a protective layer 44 to protect from scratches or other environmental damage, including mechanical or chemical damage. Protective layer 44 can be formed over just multi-layer micro-wire 50 (not shown) or over a more extensive portion of substrate surface 41 (as shown).

Figure 11:
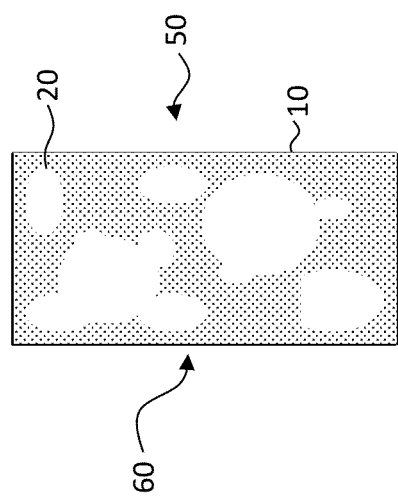
FIG. 11 is a plan view of a multi-layer micro-wire illustrating an embodiment of the present invention.

Referring to the top view of FIG. 11, a layer (second layer 20) need not continuously cover another layer, (first layer 10) in multi-layer micro-wire 50. In an embodiment, first layer 10 completely covers micro-channel 60 surface or second layer 20 or second layer 20 completely covers micro-channel 60 surface or first layer 10. Alternatively, first layer 10 covers only a portion of micro-channel 60 surface or second layer 20 or second layer 20 covers only a portion of micro-channel 60 surface or first layer 10. Micro-channel 60 surface is micro-channel sides 62 and micro-channel bottom 63 (as illustrated in FIG. 7).

In various embodiments of the present invention, multi-layer micro-wire 50 has a width less than or equal to 10 microns, 5 microns, 4 microns, 3 microns, 2 microns, or 1 micron. Likewise, micro-channel 60 has a width less than or equal to 20 microns, 10 microns, 5 microns, 4 microns, 3 microns, 2 microns, or 1 micron. In some embodiment, multi-layer micro-wire 50 can fill micro-channel 60; in other embodiments multi-layer micro-wire 50 does not fill micro-channel 60.

Figure 12:
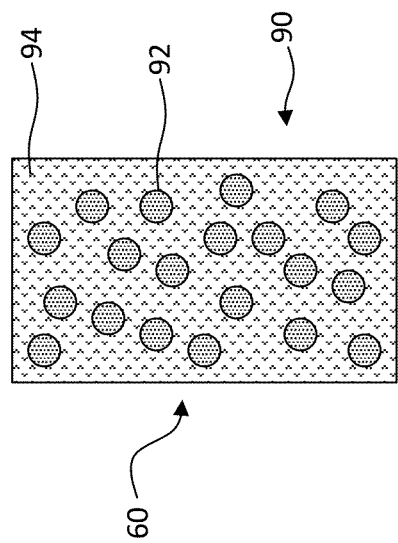
FIG. 12 is a schematic illustrating a material composition in a micro-channel useful in understanding various embodiments of the present invention.
Figure 13:
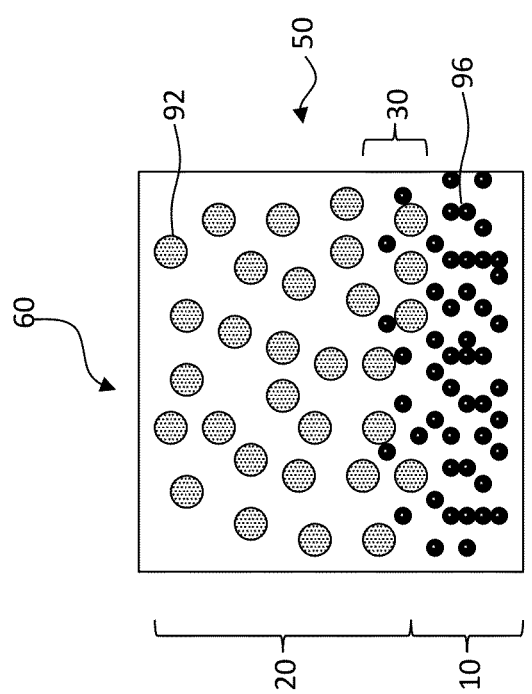
FIG. 13 is a cross section of a multi-layer micro-wire in a micro-channel illustrating an embodiment of the present invention.

In an embodiment, first or second layer 10, 20 is solid. Referring to FIG. 13, in another embodiment, first or second layer 10, 20 is porous. Referring also to FIG. 12, a material composition 90 can include conductive particles 92 (or light-absorbing particles) in a liquid carrier 94 (for example an aqueous solution). Liquid carrier 94 can be located in micro-channels 60 and heated or dried to remove liquid carrier 94, leaving a porous assemblage of conductive particles 92 that can be sintered to form a porous electrical conductor in a layer. First and second layers 10, 20 having different conductive particles 92 and light-absorbing particles 96 can overlap to form a layer (third layer 30) including both first and second material compositions, as shown in FIG. 13. Thus, in an embodiment, first and second layers 10, 20 are processed to change their material compositions, and also to form the third layer 30 having a material composition that includes materials from the first and second material compositions.

Figure 14B:
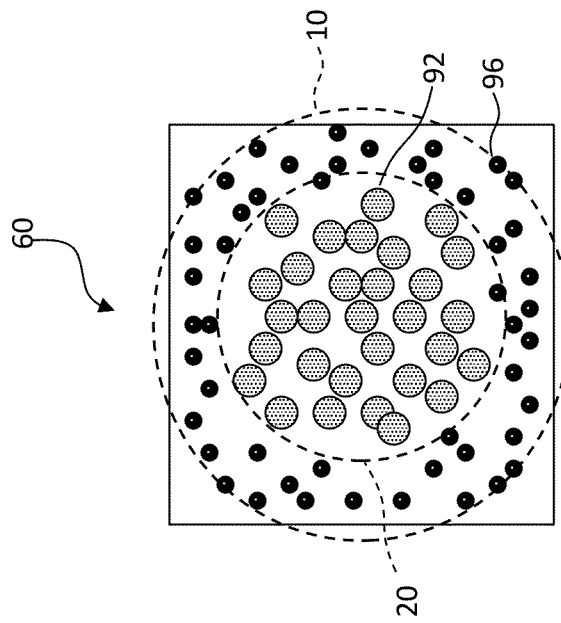
FIG. 14B is a cross section of a multi-layer micro-wire in a micro-channel illustrating an embodiment of the present invention.
Figure 14A:
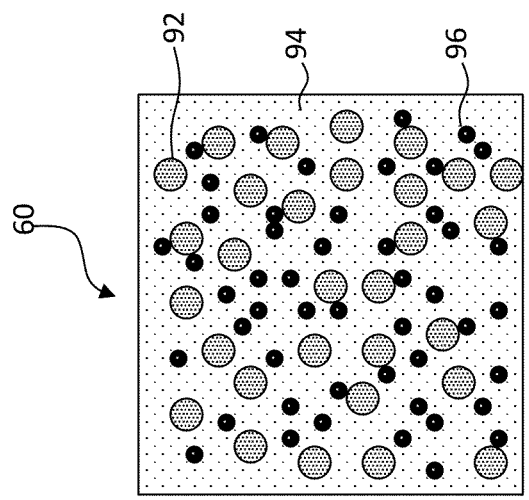
FIG. 14A is a cross section of a material composition in a micro-channel useful for understanding an embodiment of the present invention.

Referring to the example of FIGS. 14A and 14B, a material composition having conductive particles 92 and light-absorbing particles 96 in the liquid carrier 94 is located in the micro-channel 60. The material composition is processed, for example by drying and treatment with hydrochloric acid, to remove liquid carrier 94, agglomerate conductive particles 92 and move light-absorbing particles 96 outside the area of agglomerated conductive particles 92 forming a light-absorbing first layer 10 concentric with a conductive second layer 20. Conductive particles 92 can be, for example, silver nano-particles and light-absorbing particles 96 can be, for example, carbon black, a dye, or pigments. The liquid carrier 94 can be an aqueous solution and can include surfactants, humectants, thickeners, adhesives and other active chemicals. Using a commercial dye and silver nano-particles, the material composition of FIG. 14A has been processed with HCl and heat to form the layer structure of FIG. 14B, resulting in the conductive second layer 20. Although, for clarity, light-absorbing particles 96 are illustrated in a concentric ring around light-absorbing particles 96 in FIG. 14B, in practice first and second layers 10, 20 can overlap or intermingle somewhat, and such structures are included in the present invention. In embodiments of the present invention, first and second layers 10, 20 can overlap or intermingle where first and second layers 10, 20, interface, possibly forming a third layer (not shown), or have contacting surfaces, either straight or curved.

Figure 15:
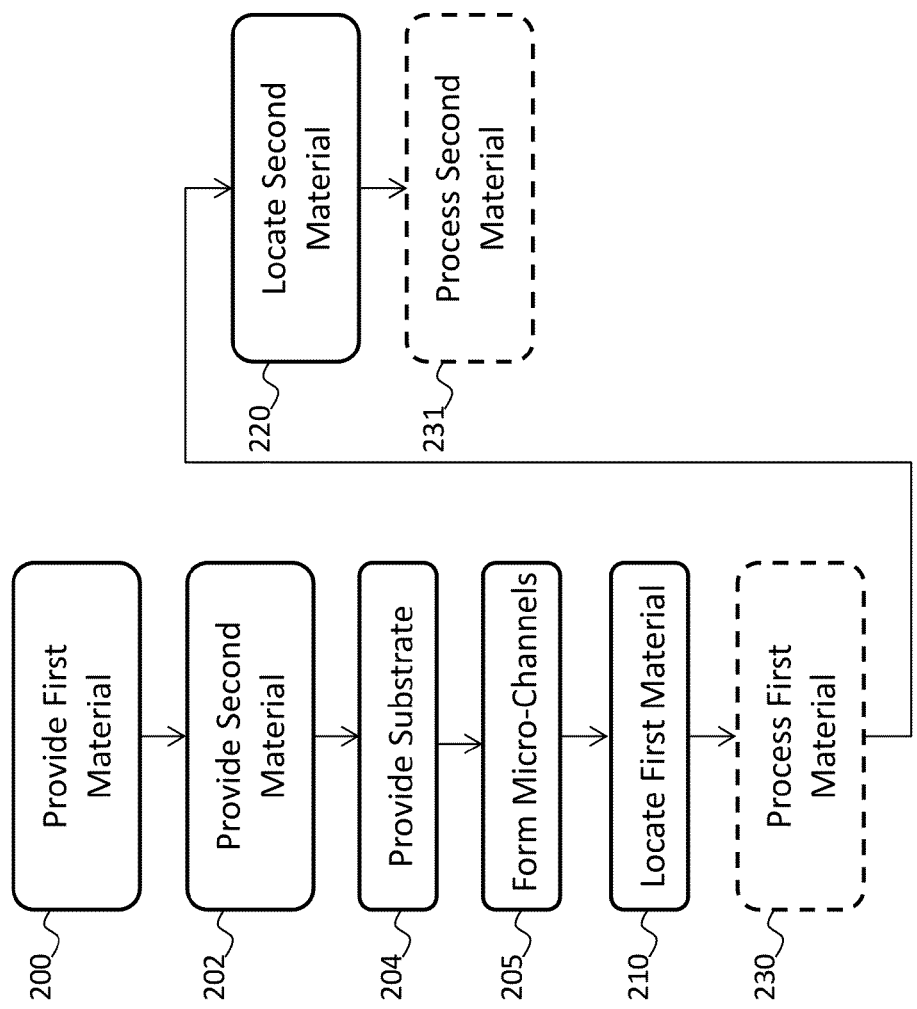

Referring to FIG. 15, a method of making the multi-layer micro-wire structure 5 according to an embodiment of the present invention includes providing (Step 200) a first material composition, providing (Step 202) a second material composition different from the first material composition, and providing (Step 204) the substrate 40 having the substrate surface 41. A plurality of micro-channels 60 are formed (Step 205) in substrate surface 41. The first material composition is located (Step 210) in the first layer 10 in each micro-channel 60 and not on substrate surface 41 and is optionally processed (Step 230) to form first layer 10. The amount of the first material composition is selected so that, when the first material composition is located and processed in micro-channel 60, first layer 10 does not fill micro-channel 60. The second material composition is located (Step 220) in a second layer 20 different from first layer 10 in each micro-channel 60 and not on substrate surface 41 and is optionally processed (Step 231) to form second layer 20. First and second layers 10, 20 can, but need not, fill micro-channel 60 or extend above substrate surface 41 (FIGS. 2, 4, 8). The amount of the second material composition is selected to fill micro-channel 60 to the desired extent. The optionally processed first material composition in first layer 10 and the optionally processed second material composition in second layer 20 form an electrically conductive multi-layer micro-wire 50 in each micro-channel 60.

The first or second material compositions can be provided (Steps 200, 202) as a liquid or as particles within a liquid carrier (as illustrated in FIG. 12). Alternatively, the first or second material compositions can be provided (Steps 200, 202) as a powder. The first or second material compositions can be provided together or before or after each other in separate process steps.

Figure 16:
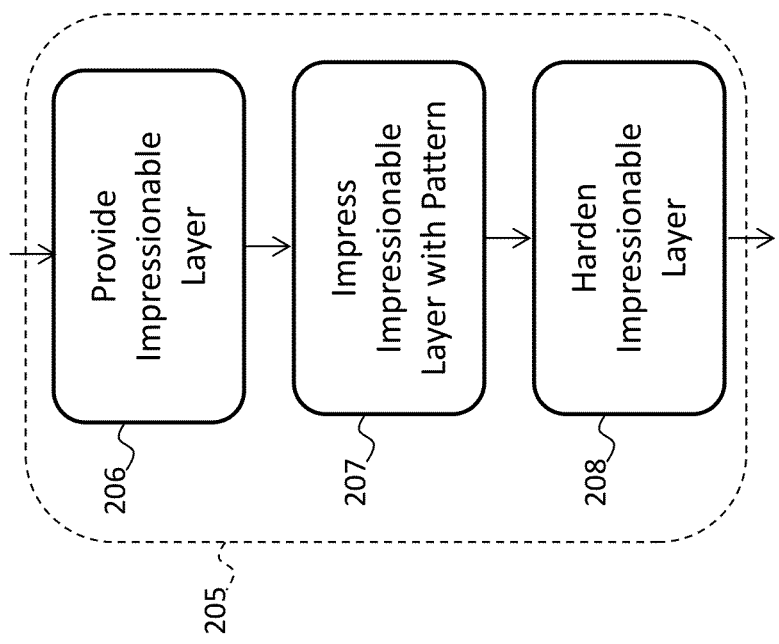

In a further method, referring to FIG. 16, the plurality of micro-channels 60 is formed (Step 205) (corresponding to (Step 205) of FIG. 15) in substrate 40 by providing (Step 206) an impressionable layer as part of substrate 40. Referring also to FIG. 7, substrates 40 can include multiple layers having different chemical or mechanical properties, for example a polymer layer 48 formed or located on a glass substrate 46. Substrate 40 can be provided in one state and then processed into another state. In particular, substrate 40 can be initially provided as the glass substrate 46 or plastic layer on which a partially cured and impressionable polymer layer 48 is formed, for example by coating. The impressionable polymer layer 48 is impressed (Step 207) with a pattern forming micro-channels 60, and then subsequently hardened (Step 208) for example by curing into a more rigid state forming the patterned polymer layer 48. Curing can be accomplished by heating or electromagnetic radiation, for example exposure to ultra-violet light. Suitable curable materials are known in the art. Alternatively, substrate 40 can be provided as a glass or plastic layer in which micro-channels 60 are etched.

Figure 17:
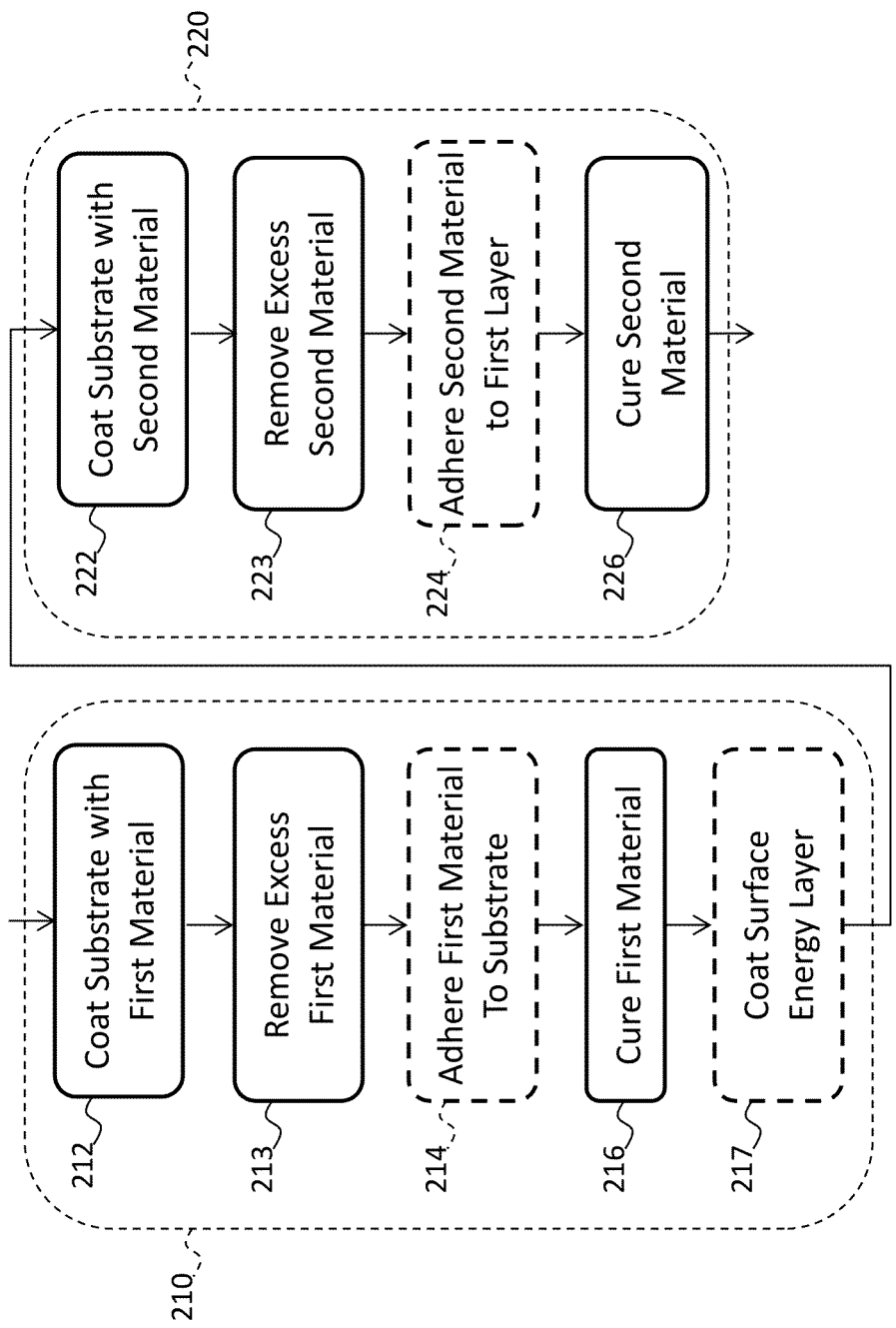

Referring to FIG. 17, a method of the present invention is illustrated in more detail. As shown in FIG. 17, locating (Step 210) a first material composition in micro-channels 60 (corresponding to Step 210 of FIG. 15) can be implemented by coating (Step 212) a first material composition over the provided substrate 40. Excess first material composition is removed (Step 213) and the remaining first material composition is optionally adhered 214 to substrate 40. The first material composition is cured (Step 216) to form first layer 10. Curing (Step 216) the first material composition and adhering (Step 214) the first material composition can be done in a common process step or separate process steps. A surface-energy layer is optionally coated (Step 217) over first layer 10 to enhance wetting of first layer 10 when substrate 40 is coated (Step 222) with the second material composition. The coated layer can include a material that controls the surface energy of the first material composition with respect to the second material composition, for example to enhance wetting of one material composition over a layer. Excess second material composition is removed (Step 223) and the remaining second material composition is optionally adhered (Step 224) to substrate 40 or first layer 10, or both. The second material composition is cured (Step 226) to form second layer 20. Curing (Step 226) the second material composition and adhering (Step 224) the second material composition can be done in a common process step or separate process steps.

Curing material compositions to form layers (first or second layers 10, 20) or adhering the layers to each other or substrate 40 (Steps 214, 216, 224, 226) can be done by drying or heating. In particular, if micro-channel 60 is formed in the polymer layer 48, heating the polymer layer 48 slightly can soften the polymer so that particles, for example black pigment or carbon black particles or conductive particles, in the first or second material compositions can adhere to the polymer. Such heating can be done by convective heating (putting substrate 40 into an oven) or by infrared radiation. Heating with infrared radiation has the advantage that light-absorbing particles, for example black particles, differentially absorb the infrared radiation and heat up more than substrate 40 (that can be transparent), thus providing a more efficient adhesion or drying process for a material composition. Adhesion of first or second layers 10, 20 to substrate 40 or to each other is advantageous because such adhered layers are more resistant to mechanical abrasion and are thus more environmentally robust.

Figure 18:
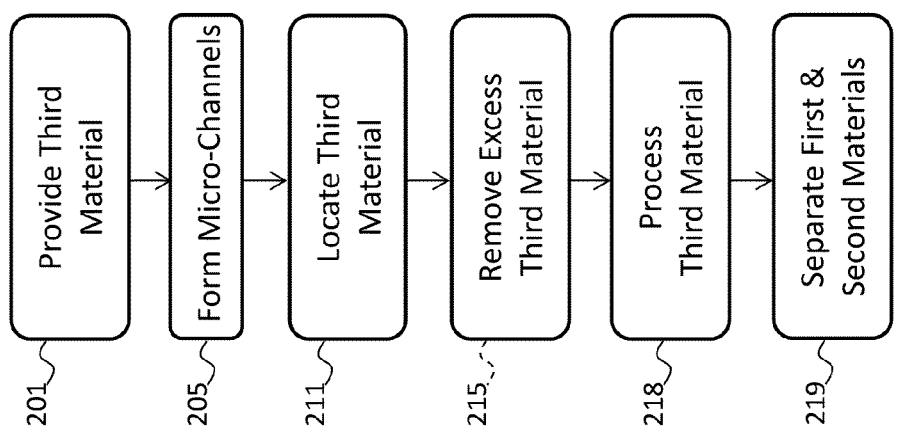

Referring to FIG. 18, in yet another embodiment of the present invention, the first and second material compositions are located in micro-channels 60 by providing (Step 201) a third material composition having the materials of the first and second material compositions and forming (Step 205) micro-channels 60 in substrate 40. The third material composition is located (Step 211) over substrate surface 41 and in micro-channels 60, for example by coating. Excess third material composition, if any, is removed (Step 215) from substrate surface 41 and not micro-channels 60. The third material composition is processed (Step 218) to separate (Step 219) the first material composition into first layer 10 and the second material composition into second layer 20, for example as illustrated in FIGS. 14A and 14B. The first and second material compositions can be cured to form first and second layers 10, 20 as a part of the separation process (Step 219) or as a separate step. In various embodiments of the present invention, curing and separation process steps are done with heat, drying, or hydrochloric acid treatment or a combination.

As noted above with respect to the first or second material compositions, the third material composition can be provided (Step 201) as a liquid or as particles within a liquid carrier (as illustrated in FIG. 12). Alternatively, the third material composition can be provided (Step 201) as a powder. Referring to FIG. 19, particles are provided (Step 250) and a carrier is provided (Step 255). The particles and carrier are combined to form (Step 260) a material composition for example providing (Steps 200, 201, 202) the first, second, or third material composition. Alternatively, referring to FIG. 20, particles are provided (Step 270) as a powder. Multiple materials can be provided and mixed in the powder and the mixture can then serve as a material composition, for example providing (Steps 200, 201, 202) the first, second, or third material composition.

The third material composition can include a wax that, when processed can separate to form a part of either first or second layers 10, 20, and provide some resistance to mechanical or chemical environmental abuse.

Conductive ink formulations useful for the present invention are commercially available, as are substrates, substrate coating methods, and micro-patterning methods for forming micro-channels. Curable polymer layers are well known as are method for coating, patterning, and curing them. Light-absorbing materials are also known and can be made into coatable material compositions using techniques known in the chemical arts.

For example, it has been demonstrated that multi-layer micro-wires 50 can be made in the substrate surface 41 embossed with micro-channels 60 by coating substrate 40 with a conductive ink including dyes or immersing substrate 40 in a bath of conductive ink including dyes, removing excess material not in micro-channels 60, and then processing substrate 40 and conductive ink with HCl and heat. In another example, a print master (for example a flexographic printing plate) having a relief pattern is coated with a conductive ink and the pattern transferred to a substrate multiple times.

Figure 21:
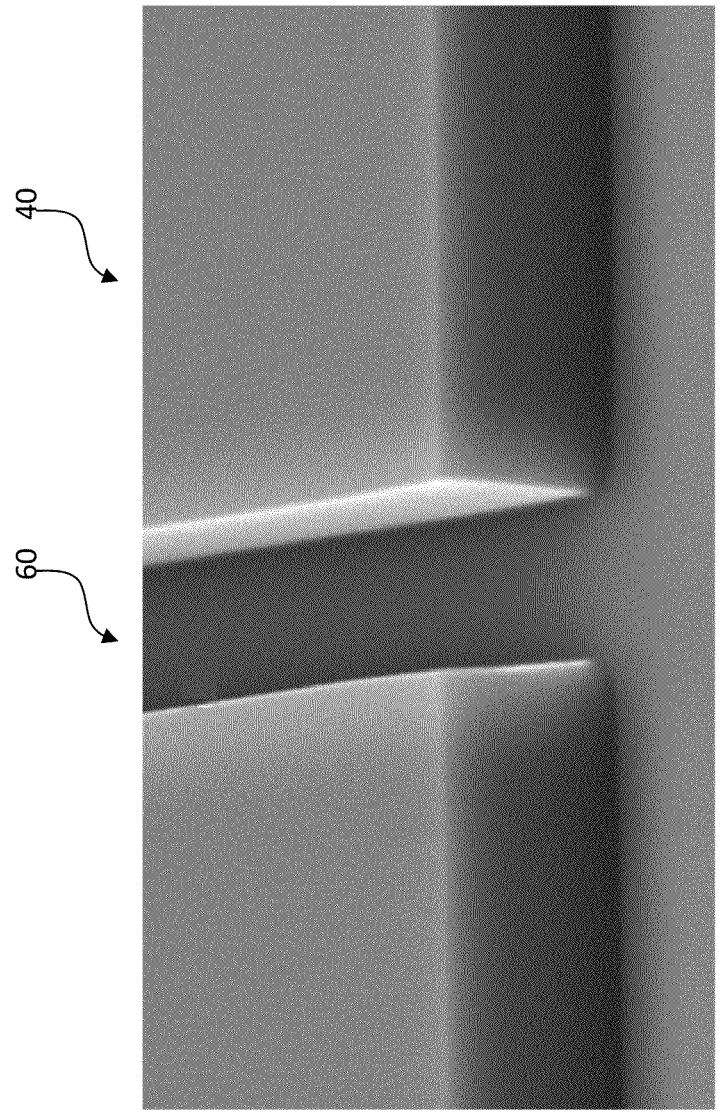
FIG. 21 is a representation of a micrograph illustrating a micro-channel useful in an embodiment of the present invention.

FIG. 21 illustrates a substrate 40 useful for the present invention having a pattern of 5µ-wide micro-channels 60 embossed therein.

Electrically conductive multi-layer micro-wire structures 5 and methods of the present invention are useful for making electrical conductors and busses for transparent micro-wire electrodes and electrical conductors in general, for example as used in busses. A variety of micro-wire patterns can be used and the present invention is not limited to any one pattern. Multi-layer micro-wires 50 can be spaced apart, form separate electrical conductors, or intersect to form a mesh electrical conductor in substrate 40 (as illustrated in FIG. 21, discussed further below). Micro-channels 60 can be identical or have different sizes, aspect ratios, or shapes. Similarly, multi-layer micro-wires 50 can be identical or have different sizes, aspect ratios, or shapes. Multi-layer micro-wires 50 can be straight or curved.

Substrate 40 can be a rigid or a flexible substrate made of, for example, a glass or polymer material, can be transparent, and can have opposing substantially parallel and extensive surfaces. Substrates 40 can include a dielectric material useful for capacitive touch screens and can have a wide variety of thicknesses, for example 10 microns, 50 microns, 100 microns, 1 mm, or more. In various embodiments of the present invention, substrates 40 are provided as a separate structure or are coated on another underlying substrate, for example by coating a polymer substrate layer on an underlying glass substrate. Such substrates 40 and their methods of construction are known in the prior art. Substrate 40 can be an element of other devices, for example the cover or substrate of a display or a substrate, cover, or dielectric layer of a touch screen. According to embodiments of the present invention, multi-layer micro-wires 50 extend across at least a portion of substrate 40 in a direction parallel to substrate surface 41 of substrate 40.

Electrically conductive micro-layer micro-wire structures 5 of the present invention are useful, for example in touch screens such as projected-capacitive touch screens that use transparent micro-wire electrodes and in displays. Electrically conductive multi-layer micro-wire structures 5 can be located in areas other than display areas, for example in the perimeter of the display area of a touch screen, where the display area is the area through which a user views a display.

Figure 22:
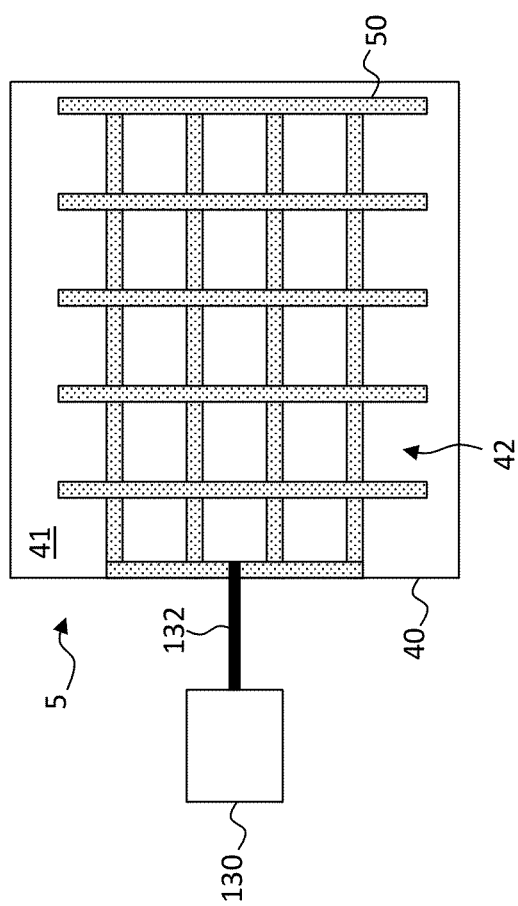
FIG. 22 is a schematic illustrating an embodiment of the present invention.

When used in display systems, micro-layer micro-wires 50 of the present invention provide an advantage in that light-absorbing layers can reduce reflection from substrate surface 41, thereby improving the contrast of a display system. At the same time, the conductive layers provide electrical conduction useful for transmitting electrical signals or forming electrical fields. Referring to FIG. 22, integrated circuit controllers 130 or power supplies electrically connected with electrical wires 132 to multi-layer micro-wires 50 provide electrical energy to multi-layer micro-wire 50. Multi-layer micro-wire 50 operates to conduct electricity or form an electrical field along the length of multi-layer micro-wire 50.

Figure 23B:
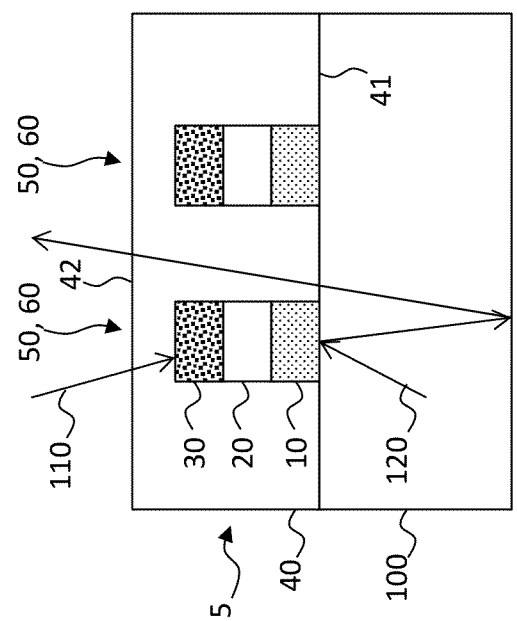
FIGS. 23A and 23B are cross sections of display systems illustrating an embodiment of the present invention.
Figure 23A:
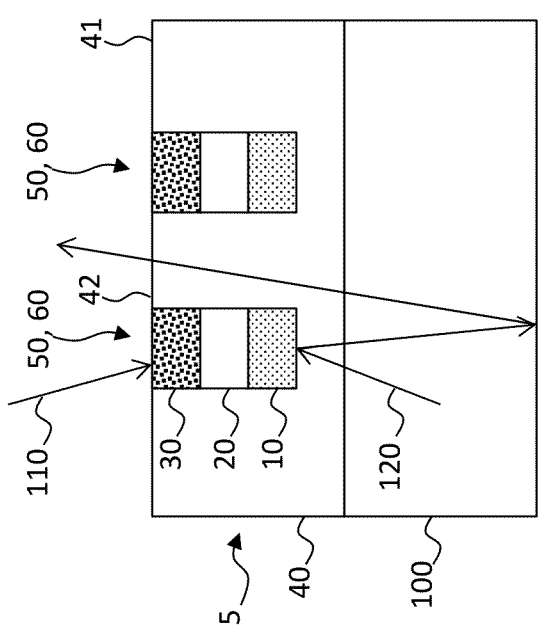

In an embodiment of the present invention, for example as illustrated in FIGS. 23A and 23B, first layer 10 can be reflective and third layer 30 can be light-absorbing. Second layer 20 is electrically conductive. As shown in FIGS. 23A and 23B, a display 100 emits light 120 that is reflected from first layer 10, reflected again from a back layer (an electrode as is commonly found in OLED devices of the prior art or a backlight as is commonly found in transmissive LCD devices of the prior art), and then emitted. In contrast, ambient light 110 is absorbed by light-absorbing third layer 30. Thus, because ambient light reflection is reduced and emitted light is increased, the arrangement of FIG. 20A improves the contrast of displays. As shown in FIG. 23A, multi-layer micro-wire structure 5 has substrate surface 41 on the side of substrate 40 opposite display 100 with light-absorbing first layer 10 at the bottom of micro-channel 60. In FIG. 23B, multi-layer micro-wire structure 5 is reversed so that substrate surface 41 is adjacent display 100 with light-absorbing first layer 10 at the top of micro-channel 60.

In an alternative embodiment, both first and third layers 10, 30 are light-absorbing. In other embodiments, a special reflective layer is omitted since metals (for example in a conductive layer) are quite reflective and only a light-absorbing layer is used in combination with a conductive layer (as illustrated in FIGS. 1 and 2).

Conductive inks including metallic particles are known in the art. In useful embodiments, the conductive inks include nano-particles, for example silver, in a carrier fluid such as an aqueous solution. The carrier fluid can include surfactants that reduce flocculation of the metal particles. Once deposited, the conductive inks are cured, for example by heating. The curing process drives out the solution and sinters the metal particles to form a metallic electrical conductor. In other embodiments, the conductive inks are powders that are pattern-wise transferred to a substrate and cured or are powders coated on a substrate and pattern-wise cured. Conductive inks are known in the art and are commercially available.

In any of these cases, conductive inks or other conducting materials are conductive after they are cured and any needed processing completed. Deposited materials are not necessarily electrically conductive before patterning or before curing. As used herein, a conductive ink is a material that is electrically conductive after any final processing is completed and the conductive ink is not necessarily conductive at any other point in multi-layer micro-wire 50 formation process.

Substrate 40 of the present invention can include any material capable of providing a supporting surface on which multi-layer micro-wires 50 can be formed and patterned. Substrates such as glass, metal, or plastic can be used and are known in the art together with methods for providing suitable surfaces. In a useful embodiment, substrate 40 is substantially transparent, for example having a transparency of greater than 90%, 80% 70% or 50% in the visible range of electromagnetic radiation.

A conductive layer of multi-layer micro-wires 50 can be metal, for example silver, gold, aluminum, nickel, tungsten, titanium, tin, or copper or various metal alloys including, for example silver, gold, aluminum, nickel, tungsten, titanium, tin, or copper. Multi-layer micro-wires 50 can include a thin metal layer composed of highly conductive metals such as gold, silver, copper, or aluminum. Other conductive metals or materials can be used. Alternatively, multi-layer micro-wires 50 can include cured or sintered metal particles such as nickel, tungsten, silver, gold, titanium, or tin or alloys such as nickel, tungsten, silver, gold, titanium, or tin. Conductive inks can be used to form multi-layer micro-wires 50 with pattern-wise deposition or pattern-wise formation followed by curing steps. Other materials or methods for forming multi-layer micro-wires 50 can be employed and are included in the present invention.

In an example and non-limiting embodiment of the present invention, each multi-layer micro-wire 50 is from 5 microns wide to one micron wide and is separated from neighboring micro-wires 50 by a distance of 20 microns or less, for example 10 microns, 5 microns, 2 microns, or one micron.

Methods and device for forming and providing substrates, coating substrates, patterning coated substrates, or pattern-wise depositing materials on a substrate are known in the photo-lithographic arts. Likewise, tools for laying out electrodes, conductive traces, and connectors are known in the electronics industry as are methods for manufacturing such electronic system elements. Hardware controllers for controlling touch screens and displays and software for managing display and touch screen systems are all well known. All of these tools and methods can be usefully employed to design, implement, construct, and operate the present invention. Methods, tools, and devices for operating capacitive touch screens can be used with the present invention.

The present invention is useful in a wide variety of electronic devices. Such devices can include, for example, photovoltaic devices, OLED displays and lighting, LCD displays, plasma displays, inorganic LED displays and lighting, electrophoretic displays, electrowetting displays, dimming mirrors, smart windows, transparent radio antennae, transparent heaters and other touch screen devices such as resistive touch screen devices.

The invention has been described in detail with particular reference to certain embodiments thereof, but it will be understood that variations and modifications can be effected within the spirit and scope of the invention.

PARTS LIST

D depth
D1 first layer depth
D2 second layer depth
D3 depth
D4 depth
W width
5 multi-layer micro-wire structure
10 first layer
11 location
12 location
20 second layer
30 third layer
40 substrate 41 substrate surface
42 substrate-surface open area
44 protective layer
46 glass substrate
48 polymer layer
50 multi-layer micro-wire
60 micro-channel
61 micro-channel top
62 micro-channel side
63 micro-channel bottom
70 flat surface
72 curved surface
74 extended surface
80 surface-energy layer
82 adhesion layer
90 material composition
92 conductive particles
94 carrier
96 light-absorbing particles
100 display
110 ambient light
120 emitted light
130 integrated circuit controller
132 electrical wire
200 provide first material composition step
201 provide third material composition step
202 provide second material composition step
204 provide substrate step
205 form micro-channels step
206 provide impressionable layer step
207 impress impressionable layer with pattern step
208 harden impressionable layer step
210 locate first material step
211 located third material step
212 coat substrate with first material step
213 remove excess first material step
214 optional adhere first material to substrate step
215 optional remove excess third material step
216 cure first material step
217 optional coat surface-energy layer step
218 process third material step
219 separate first and second materials step
220 locate second material step
222 coat substrate with second material step
223 remove excess second material step
224 optional adhere second material to first layer step
226 cure second material step
230 optional process first material composition step
231 optional process second material composition step
250 provide particles step
255 provide carrier step
260 form material composition step
270 provide particles step

The invention claimed is:

1. A method of making a multi-layer micro-wire structure, comprising:
  providing a substrate having a surface;
  forming a plurality of micro-channels in the substrate;
  locating a first material composition in a first layer only in each micro-channel and not on the substrate surface by coating the first material composition over the substrate surface and micro-channels, removing the first material composition from the substrate surface and not the micro-channels, and curing the first material composition into the first layer;
  locating a second material composition different from the first material composition in a second layer different from and in contact with the first layer only in each micro-channel and not on the substrate surface by coating the second material composition over the substrate surface, first layer, and micro-channels, removing the second material composition from the substrate surface and not the micro-channels or first layer, and curing the second material composition into the second layer; and
  wherein:
    the first layer and the second layer have different structures;
    the first material composition in the first layer is electrically conductive and the second material composition in the second layer is electrically conductive; and
    the first material composition in the first layer and the second material composition in the second layer form an electrically conductive multi-layer micro-wire in each micro-channel.

2. The method of claim 1, further including forming the first or second layer with a variable thickness.

3. The method of claim 1, further including forming the first layer thicker than the second layer.

4. The method of claim 1, further including forming the first or second layer so that the first layer is not exclusively over or under the second layer or so that the second layer is not exclusively over or under the first layer.

5. The method of claim 1, further including forming the first layer so that it overlaps or intermingles with the second layer.

6. The method of claim 1, further including forming the first and second layers in contact over a substantially flat surface.

7. The method of claim 1, further including forming the first and second layers in contact over a substantially curved surface.

8. The method of claim 1, further including forming the first and second layers so that the first and second layers do not fill the micro-channels.

9. The method of claim 1, further including forming the first and second layers so that the first and second layers fill the micro-channels.

10. The method of claim 1, further including forming the first and second layers so that the first or second layer extends above the substrate surface.

11. A method of making a multi-layer micro-wire structure, comprising:
  providing a substrate having a surface;
  forming a plurality of micro-channels in the substrate;
  locating a first material composition in a first layer only in each micro-channel and not on the substrate surface by coating the first material composition over the substrate surface and micro-channels, removing the first material composition from the substrate surface and not the micro-channels, and curing the first material composition into the first layer;
  locating a second material composition different from the first material composition in a second layer different from and in contact with the first layer only in each micro-channel and not on the substrate surface by coating the second material composition over the substrate surface, first layer, and micro-channels, removing the second material composition from the substrate surface and not the micro-channels or first layer, and curing the second material composition into the second layer; and
  wherein:
    the first layer and the second layer have different material attributes;

the first material composition in the first layer is electrically conductive and the second material composition in the second layer is electrically conductive; and the first material composition in the first layer and the second material composition in the second layer form an electrically conductive multi-layer micro-wire in each micro-channel.

12. The method of claim 11, further including providing the first material composition with two different materials in a first ratio and the second material composition with the same two materials in a second ratio different from the first ratio.

13. The method of claim 11, further including providing the first material composition with an electrical conductivity that is different from the electrical conductivity of the second material composition.

14. The method of claim 11, further including providing the first material composition with an optical property that is different from the optical property of the second material composition.

15. The method of claim 14, wherein the optical property is light-absorption.

\* \* \* \* \*